US010660725B2

(12) United States Patent
Baril et al.

(10) Patent No.: US 10,660,725 B2
(45) Date of Patent: May 26, 2020

(54) ENDOSCOPIC SURGICAL CLIP APPLIER INCLUDING COUNTER ASSEMBLY

(71) Applicant: Covidien LP, Mansfield, MA (US)

(72) Inventors: Jacob C. Baril, White Plains, NY (US); Brandon L. Calavan, Windsor, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 252 days.

(21) Appl. No.: 15/863,400

(22) Filed: Jan. 5, 2018

(65) Prior Publication Data

US 2018/0228567 A1    Aug. 16, 2018

Related U.S. Application Data

(60) Provisional application No. 62/458,601, filed on Feb. 14, 2017.

(51) Int. Cl.
*A61B 17/128* (2006.01)
*A61B 17/10* (2006.01)
(Continued)

(52) U.S. Cl.
CPC .............. *A61B 90/08* (2016.02); *A61B 17/10* (2013.01); *A61B 17/1285* (2013.01);
(Continued)

(58) Field of Classification Search
CPC ... A61B 17/10; A61B 17/128; A61B 17/1285; A61B 2017/00407; A61B 2017/00115;
(Continued)

(56) References Cited

U.S. PATENT DOCUMENTS 3,120,230 A    2/1964  Skold
3,363,628 A    1/1968  Wood
(Continued)

FOREIGN PATENT DOCUMENTS

AU    2013254887 A1    11/2013
CA       1163889 A      3/1984
(Continued)

OTHER PUBLICATIONS

European Office Action corresponding to European Appln. No. EP 16 15 9324.9 dated Aug. 7, 2017.
(Continued)

*Primary Examiner* — Katrina M Stransky

(57) ABSTRACT

A counter assembly is supported in a handle assembly of a clip applier. The counter assembly includes a counting mechanism, a ratchet mechanism, and an actuator. The counting mechanism is positioned to rotate within the handle assembly and includes indicia visible through the handle assembly. The ratchet mechanism is rotationally coupled to the counting mechanism and prohibits multidirectional rotation of the counting mechanism. The actuator includes a protrusion projecting therefrom. The actuator is positioned to translate between a proximal position and a distal position, wherein the protrusion of the actuator engages the counting mechanism to rotate the counting mechanism, in a first direction, to adjust the indicia of the counting mechanism, which is visible through the handle assembly. In the proximal position, the protrusion of the actuator is disposed proximal of the counting mechanism. In the distal position, the protrusion of the actuator is disposed distal of the counting mechanism.

17 Claims, 6 Drawing Sheets

(51) Int. Cl.
*A61B 17/00* (2006.01)
*A61B 90/00* (2016.01)

(52) U.S. Cl.
CPC .............. *A61B 17/00234* (2013.01); *A61B 2017/00115* (2013.01); *A61B 2017/00407* (2013.01); *A61B 2090/0803* (2016.02); *A61B 2090/0814* (2016.02)

(58) Field of Classification Search
CPC .......... A61B 2090/0803; A61B 17/068; A61B 2090/0814; A61B 2017/2929; A61B 17/083; A61B 17/105; A61B 2017/00473; A61B 2017/00477; A61B 2090/0807; A61B 17/0682; A61B 2090/0813
See application file for complete search history.

(56) References Cited

U.S. PATENT DOCUMENTS

| | | | |
|---|---|---|---|
| 3,638,847 | A | 2/1972 | Noiles et al. |
| 3,675,688 | A | 7/1972 | Bryan et al. |
| 3,735,762 | A | 5/1973 | Bryan et al. |
| 3,867,944 | A | 2/1975 | Samuels |
| 4,242,902 | A | 1/1981 | Green |
| 4,296,751 | A | 10/1981 | Blake, III et al. |
| 4,372,316 | A | 2/1983 | Blake, III et al. |
| 4,408,603 | A | 10/1983 | Blake, III et al. |
| 4,412,539 | A | 11/1983 | Jarvik |
| 4,418,694 | A | 12/1983 | Beroff et al. |
| 4,471,780 | A | 9/1984 | Menges et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A | 4/1985 | McGarry et al. |
| 4,512,345 | A | 4/1985 | Green |
| 4,522,207 | A | 6/1985 | Klieman et al. |
| 4,532,925 | A | 8/1985 | Blake, III |
| 4,534,351 | A | 8/1985 | Rothfuss et al. |
| 4,545,377 | A | 10/1985 | Cerwin et al. |
| 4,549,544 | A | 10/1985 | Favaron |
| 4,556,058 | A | 12/1985 | Green |
| 4,557,263 | A | 12/1985 | Green |
| 4,562,839 | A | 1/1986 | Blake, III et al. |
| 4,572,183 | A | 2/1986 | Juska |
| 4,576,165 | A | 3/1986 | Green et al. |
| 4,576,166 | A | 3/1986 | Montgomery et al. |
| 4,590,937 | A | 5/1986 | Deniega |
| 4,598,711 | A | 7/1986 | Deniega |
| 4,602,631 | A | 7/1986 | Funatsu |
| 4,611,595 | A | 9/1986 | Klieman et al. |
| 4,612,932 | A | 9/1986 | Caspar et al. |
| 4,616,650 | A | 10/1986 | Green et al. |
| 4,616,651 | A | 10/1986 | Golden |
| 4,624,254 | A | 11/1986 | McGarry et al. |
| 4,637,395 | A | 1/1987 | Caspar et al. |
| 4,646,740 | A | 3/1987 | Peters et al. |
| 4,647,504 | A | 3/1987 | Kimimura et al. |
| 4,658,822 | A | 4/1987 | Kees, Jr. |
| 4,660,558 | A | 4/1987 | Kees, Jr. |
| 4,662,373 | A | 5/1987 | Montgomery et al. |
| 4,662,374 | A | 5/1987 | Blake, III |
| 4,671,278 | A | 6/1987 | Chin |
| 4,671,282 | A | 6/1987 | Tretbar |
| 4,674,504 | A | 6/1987 | Klieman et al. |
| 4,681,107 | A | 7/1987 | Kees, Jr. |
| 4,696,396 | A | 9/1987 | Samuels |
| 4,702,247 | A | 10/1987 | Blake, III et al. |
| 4,706,668 | A | 11/1987 | Backer |
| 4,712,549 | A | 12/1987 | Peters et al. |
| 4,733,666 | A | 3/1988 | Mercer, Jr. |
| 4,759,364 | A | 7/1988 | Boebel |
| 4,765,335 | A | 8/1988 | Schmidt et al. |
| 4,777,949 | A | 10/1988 | Perlin |
| 4,796,625 | A | 1/1989 | Kees, Jr. |
| 4,799,481 | A | 1/1989 | Transue et al. |
| 4,815,466 | A | 3/1989 | Perlin |
| 4,821,721 | A | 4/1989 | Chin et al. |
| 4,822,348 | A | 4/1989 | Casey |
| 4,834,096 | A | 5/1989 | Oh et al. |
| 4,850,355 | A | 7/1989 | Brooks et al. |
| 4,854,317 | A | 8/1989 | Braun |
| 4,856,517 | A | 8/1989 | Collins et al. |
| 4,929,239 | A | 5/1990 | Braun |
| 4,931,058 | A | 6/1990 | Cooper |
| 4,934,364 | A | 6/1990 | Green |
| 4,957,500 | A | 9/1990 | Liang et al. |
| 4,966,603 | A | 10/1990 | Focelle et al. |
| 4,967,949 | A | 11/1990 | Sandhaus |
| 4,983,176 | A | 1/1991 | Cushman et al. |
| 4,988,355 | A | 1/1991 | Leveen et al. |
| 5,002,552 | A | 3/1991 | Casey |
| 5,026,379 | A | 6/1991 | Yoon |
| 5,030,224 | A | 7/1991 | Wright et al. |
| 5,030,226 | A | 7/1991 | Green et al. |
| 5,032,127 | A | 7/1991 | Frazee et al. |
| 5,035,692 | A | 7/1991 | Lyon et al. |
| 5,047,038 | A | 9/1991 | Peters et al. |
| 5,049,152 | A | 9/1991 | Simon et al. |
| 5,049,153 | A | 9/1991 | Nakao et al. |
| 5,053,045 | A | 10/1991 | Schmidt et al. |
| 5,059,202 | A | 10/1991 | Liang et al. |
| 5,062,563 | A | 11/1991 | Green et al. |
| 5,062,846 | A | 11/1991 | Oh et al. |
| 5,078,731 | A | 1/1992 | Hayhurst |
| 5,084,057 | A | 1/1992 | Green et al. |
| 5,100,416 | A | 3/1992 | Oh et al. |
| 5,100,420 | A | 3/1992 | Green et al. |
| 5,104,394 | A | 4/1992 | Knoepfler |
| 5,104,395 | A | 4/1992 | Thornton et al. |
| 5,112,343 | A | 5/1992 | Thornton |
| 5,122,150 | A | 6/1992 | Puig |
| 5,127,915 | A | 7/1992 | Mattson |
| 5,129,885 | A | 7/1992 | Green et al. |
| 5,156,608 | A | 10/1992 | Troidl et al. |
| 5,160,339 | A | 11/1992 | Chen et al. |
| 5,163,945 | A | 11/1992 | Ortiz et al. |
| 5,171,247 | A | 12/1992 | Hughett et al. |
| 5,171,249 | A | 12/1992 | Stefanchik et al. |
| 5,171,250 | A | 12/1992 | Yoon |
| 5,171,251 | A | 12/1992 | Bregen et al. |
| 5,171,252 | A | 12/1992 | Friedland |
| 5,171,253 | A | 12/1992 | Klieman |
| 5,192,288 | A | 3/1993 | Thompson et al. |
| 5,197,970 | A | 3/1993 | Green et al. |
| 5,199,566 | A | 4/1993 | Ortiz et al. |
| 5,201,746 | A | 4/1993 | Shichman |
| 5,201,900 | A | 4/1993 | Nardella |
| 5,207,691 | A | 5/1993 | Nardella |
| 5,207,692 | A | 5/1993 | Kraus et al. |
| 5,217,473 | A | 6/1993 | Yoon |
| 5,219,353 | A | 6/1993 | Garvey, III et al. |
| 5,246,450 | A | 9/1993 | Thornton et al. |
| 5,269,792 | A | 12/1993 | Kovac et al. |
| 5,281,228 | A | 1/1994 | Wolfson |
| 5,282,807 | A | 2/1994 | Knoepfler |
| 5,282,808 | A | 2/1994 | Kovac et al. |
| 5,282,832 | A | 2/1994 | Toso et al. |
| 5,289,963 | A | 3/1994 | McGarry et al. |
| 5,290,299 | A | 3/1994 | Fain et al. |
| 5,300,081 | A | 4/1994 | Young et al. |
| 5,304,183 | A | 4/1994 | Gourlay et al. |
| 5,306,280 | A | 4/1994 | Bregen et al. |
| 5,306,283 | A | 4/1994 | Conners |
| 5,312,426 | A | 5/1994 | Segawa et al. |
| 5,330,442 | A | 7/1994 | Green et al. |
| 5,330,487 | A | 7/1994 | Thornton et al. |
| 5,340,360 | A | 8/1994 | Stefanchik |
| 5,342,373 | A | 8/1994 | Stefanchik et al. |

(56) References Cited

U.S. PATENT DOCUMENTS

| | | |
|---|---|---|
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sheds et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |

(56) References Cited

U.S. PATENT DOCUMENTS

| | | |
|---|---|---|
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |

(56) References Cited

U.S. PATENT DOCUMENTS

| | | |
|---|---|---|
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,887,553 B2 | 2/2011 | Lehman et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |

(56) References Cited

U.S. PATENT DOCUMENTS

| | | |
|---|---|---|
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,820 B2 | 9/2016 | Whiting |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,517,064 B2 | 12/2016 | Sarradon |
| 9,526,501 B2 | 12/2016 | Malkowski |
| 9,545,254 B2 | 1/2017 | Sorrentino et al. |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0235440 A1* | 10/2006 | Huitema ............... A61B 17/10 606/142 |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | A. Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |

(56) References Cited

U.S. PATENT DOCUMENTS

| | | |
|---|---|---|
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0137323 A1* | 6/2011 | Malkowski .......... A61B 17/068 606/143 |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1* | 5/2013 | Hartoumbekis ... A61B 17/1285 606/143 |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0045816 A1 | 2/2015 | Aranyi et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0 406 724 A1 | 1/1991 |
| EP | 0514139 A2 | 11/1992 |
| EP | 0514139 A3 | 3/1993 |
| EP | 0 732 078 A2 | 9/1996 |
| EP | 1769757 A1 | 4/2007 |
| GB | 2073022 A | 10/1981 |
| JP | 2003-033361 A | 2/2003 |
| JP | 2006-154230 A | 6/2006 |
| JP | 2006-277221 A | 10/2006 |
| JP | 2008-017876 A | 1/2008 |
| WO | 0042922 A1 | 7/2000 |
| WO | 2001-66001 A2 | 9/2001 |
| WO | 2001-67965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Chinese First Office Action corresponding to Chinese Appln. No. CN 2014104295806 dated Aug. 31, 2017.

Extended European Search Report corresponding to European Appln. No. EP 17 17 3508.7 dated Sep. 29, 2017.

Chinese Second Office Action corresponding to Chinese Appln. No. CN 201410076318.8 dated Oct. 10, 2017.

Extended European Search Report corresponding to European Appln. No. EP 17 18 0570.8 dated Dec. 6, 2017.

Extended European Search Report corresponding to counterpart Patent Appln. EP 18 15 6458.4 dated Sep. 3, 2018.

Extended European Search Report corresponding to European Application No. EP 07 25 3905.9, completed Jan. 29, 2008; dated Feb. 7, 2008; (7 Pages).

International Search Report corresponding to International Application No. PCT-US08-58185, completed Sep. 4, 2008; dated Sep. 9, 2008; (2 Pages).

International Search Report corresponding to International Application No. PCT-US08-59859, completed Sep. 14, 2008; dated Sep. 18, 2008; (2 Pages).

Extended European Search Report corresponding to European Application No. EP 07 25 3807.7, completed Nov. 7, 2008; dated Nov. 26, 2008; (11 Pages).

Extended European Search Report corresponding to European Application No. EP 09 25 2049.3, completed Dec. 11, 2009; dated Jan. 12, 2010; (3 Pages).

Extended European Search Report corresponding to European Application No. EP 09 25 2050.1, completed Dec. 23, 2009; dated Jan. 21, 2010; (3 Pages).

Extended European Search Report corresponding to European Application No. EP 09 25 2051.9, completed Dec. 21, 2009; dated Jan. 28, 2010; (3 Pages).

Extended European Search Report corresponding to European Application No. EP 09 25 2052.7, completed Nov. 16, 2009; dated Nov. 24, 2009; (3 Pages).

Extended European Search Report corresponding to European Application No. EP 09 25 2053.5, completed Nov. 24, 2009; dated Dec. 1, 2009; (3 Pages).

(56) References Cited

OTHER PUBLICATIONS

Extended European Search Report corresponding to European Application No. EP 09 25 2054.3, completed Jan. 7, 2010; dated Jan. 22, 2010; (3 Pages).
Extended European Search Report corresponding to European Application No. EP 09 25 2056.8, completed Jan. 8, 2010; dated Feb. 5, 2010; (3 Pages).
Extended European Search Report corresponding to European Application No. EP 10 25 0497.4, completed May 4, 2010; dated May 12, 2010; (6 Pages).
Extended European Search Report corresponding to European Application No. EP 10 25 2079.8, completed Mar. 8, 2011; dated Mar. 17, 2011; (3 Pages).
European Search Report corresponding to European Application No. EP 05 81 0218.7, completed Apr. 18, 2011; dated May 20, 2011; (3 pages).
European Search Report corresponding to European Application No. EP 05 80 7612.6, completed May 2, 2011; dated May 20, 2011; (3 pages).
Extended European Search Report corresponding to European Application No. EP 10 25 1737.2, completed May 9, 2011; dated May 20, 2011; (4 pages).
Extended European Search Report corresponding to European Application No. EP 11 25 0214.1, completed May 25, 2011; dated Jun. 1, 2011; (3 Pages).
Extended European Search Report corresponding to European Application No. EP 11 00 2681.2, completed May 31, 2011; dated Jun. 10, 2011; (3 Pages).
European Search Report corresponding to European Application No. EP 05 80 26865, completed Jan. 9, 2012; dated Jan. 18, 2012; (3 Pages).
Extended European Search Report corresponding to European Application No. EP 12 15 1313.9, completed Mar. 20, 2012 and dated Apr. 12, 2012; (5 Pages).
Extended European Search Report corresponding to European Application No. EP 12 16 1291.5, completed Apr. 24, 2012 and dated May 4, 2012; (5 Pages).
Extended European Search Report corresponding to European Application No. EP 12 16 5891.8, completed Jun. 12, 2012 and dated Jun. 20, 2012; (6 Pages).
Extended European Search Report corresponding to European Application No. EP 12 16 2288.0, completed Jun. 4, 2012 and dated Jul. 7, 2012; (6 Pages).
Extended European Search Report corresponding to European Application No. EP 12 16 4955.2, completed Aug. 23, 2012 and dated Sep. 4, 2012; (5 Pages).
Extended European Search Report corresponding to European Application No. EP 11 25 0754.6, completed Oct. 22, 2012 and dated Oct. 31, 2012; (6 Pages).
Extended European Search Report corresponding to European Application No. EP 12 18 6401.1, completed Nov. 22, 2012 and dated Nov. 30, 2012; (7 Pages).
Extended European Search Report corresponding to European Application No. EP 12 18 6448.2, completed Nov. 28, 2012 and dated Dec. 10, 2012; (6 Pages).
Extended European Search Report corresponding to European Application No. EP 12 19 1706.6, completed Dec. 19, 2012 and dated Jan. 8, 2013; (6 Pages).
Extended European Search Report corresponding to EP 12 19 8745.7, completed Mar. 19, 2013 and dated Apr. 11, 2013; (8 Pages).
Extended European Search Report corresponding to EP 12 15 2989.5, completed Apr. 9, 2013 and dated Apr. 18, 2013; (9 Pages).
Extended European Search Report corresponding to EP 08 73 2820.9, completed Jul. 2, 2013 and dated Jul. 9, 2013; (10 Pages).
Extended European Search Report corresponding to EP 13 17 2008.8, completed Aug. 14, 2013 and dated Aug. 28, 2013; (8 Pages).
Extended European Search Report corresponding to EP 13 16 6382.5, completed Nov. 19, 2013 and dated Nov. 28, 2013; (8 Pages).
Extended European Search Report corresponding to EP 11 25 0194.5, completed Nov. 25, 2013 and dated Dec. 3, 2013; (8 Pages).
Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.

(56) References Cited

OTHER PUBLICATIONS

Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart In'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

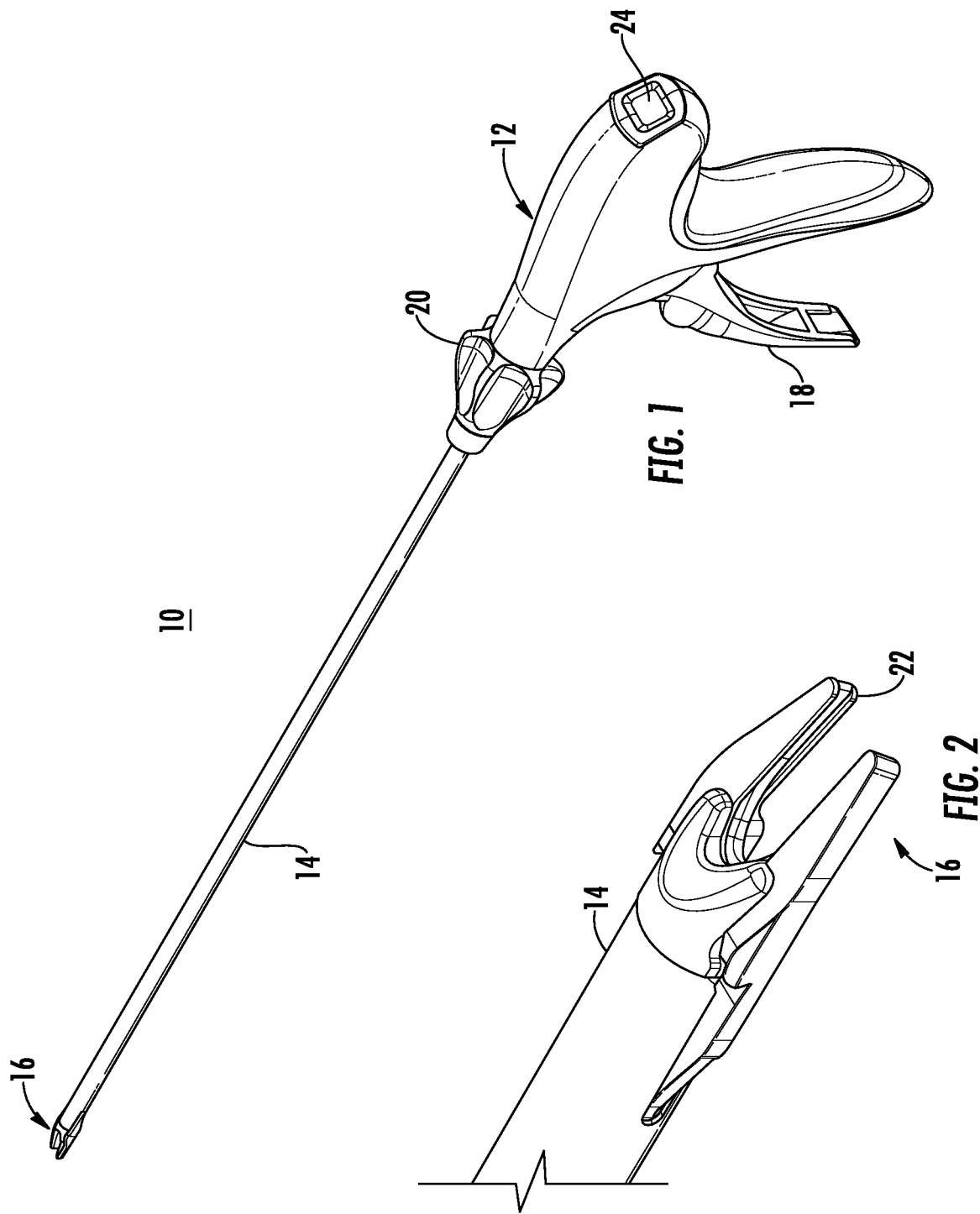

ENDOSCOPIC SURGICAL CLIP APPLIER INCLUDING COUNTER ASSEMBLY

CROSS-REFERENCE TO RELATED APPLICATIONS

This application claims the benefit of and priority to U.S. Provisional Patent Application No. 62/458,601 filed Feb. 14, 2017, the entire disclosure of which is incorporated by reference herein.

BACKGROUND

Technical Field

The presented disclosure relates generally to surgical clip appliers. More particularly, the present disclosure relates to an endoscopic surgical clip applier having a counter assembly.

Discussion of Related Art

Surgical clip appliers offer surgeons an alternative to conventional suturing of body tissues and vessels. Surgical clip appliers generally store a plurality of clips which are fed sequentially to a jaw mechanism at the distal end of the instrument upon opening and closing of handles at the proximal end of the instrument. As the handles are closed, the jaw members close to deform a clip positioned between the jaw members, and as the jaw members are opened to release the deformed clip, a new clip is fed from the plurality of clips to a position between the jaw members. This process is repeated until all the clips in the plurality of clips have been used.

A need exists for a user of the clip applier to know how many clips remain in the clip applier and/or to know when a final clip of the plurality of clips has been fired.

SUMMARY

The presented disclosure relates to endoscopic surgical clip appliers having a counter assembly.

According to an aspect of the present disclosure a surgical clip applier is provided including a handle assembly, an elongated tubular member, a rack bar, and a counter assembly. The elongated tubular member extends distally from the handle assembly. The rack bar is translatably supported in the handle assembly. The counter assembly is supported in the handle assembly. The counter assembly includes a counting mechanism, a ratchet mechanism, and an actuator. The counting mechanism is positioned to rotate within the handle assembly and includes indicia visible through the handle assembly. The ratchet mechanism is rotationally coupled to the counting mechanism. The ratchet mechanism prohibits multidirectional rotation of the counting mechanism. The actuator is supported on the rack bar for translation therewith. The actuator includes a protrusion projecting therefrom. The actuator is positioned to translate between a proximal position and a distal position. The protrusion of the actuator engages the counting mechanism to rotate the counting mechanism, in a first direction, to adjust the indicia of the counting mechanism that is visible through the handle assembly. In the proximal position, the protrusion of the actuator is disposed proximal of the counting mechanism. In the distal position, the protrusion of the actuator is disposed distal of the counting mechanism.

In some embodiments, a plurality of surgical clips is disposed within the elongated tubular member. The indicia of the counting mechanism may indicate a remaining number of the plurality of surgical clips. In one embodiment, the indicia include a plurality of numbers to indicate the remaining number of surgical clips of the plurality of surgical clips. In another embodiment, the indicia include a color to indicate the remaining number of surgical clips of the plurality of surgical clips.

The counter assembly may further include a housing. The housing may define a window through which the indicia of the counting mechanism are visible during use of the surgical clip applier. The counter mechanism may also further include a counter wheel including a plurality of actuation features circumferentially positioned thereabout, and a plurality of inner teeth formed circumferentially about an aperture defined through the counter wheel. The indicia may be disposed circumferentially about the counter wheel.

The ratchet mechanism may include a turning cap, a shaft, and a spring. The turning cap may include a plurality of teeth circumferentially positioned thereabout. The shaft may extend from the turning cap and may include a pair of radially projecting protrusions. The spring may be supported on the shaft. The ratchet mechanism may be positioned within the counter wheel of the counting mechanism, wherein the plurality of inner teeth of the counting mechanism may selectively engage with the plurality of teeth of the ratchet mechanism. The housing of the counter assembly may define an aperture therein. The aperture may define an outer transverse cross-sectional profile that is complimentary to an outer transverse cross-sectional profile of the shaft and the pair of protrusions. The engagement of the plurality of inner teeth of the counting mechanism and the plurality of teeth of the ratchet mechanism, together with the positioning of the shaft including the protrusions within the aperture of the housing, may prohibit multidirectional rotation of the counting mechanism.

In one embodiment of the present disclosure, a blocking mechanism coupled to the housing of the counter assembly. The blocking mechanism may hinder the rotation of the counting mechanism after a set number of rotations.

The actuator may flex when the actuator translates between the proximal position and the distal position as the protrusion thereof engages the counting mechanism and moves distally or proximally beyond the counting mechanism. The actuator may provide a tactile or audible feedback to a user upon the actuator unflexing while translating between the proximal position and the distal position.

According to another aspect of the present disclosure, the surgical clip applier includes a handle assembly, a rack bar, and a counter assembly. The rack bar is translatably supported in the handle assembly. The counter assembly is supported in the handle assembly. The counter assembly includes a housing, a counting mechanism, a ratchet mechanism, and an actuator. The housing defines an aperture having a non-circular profile. The counting mechanism is positioned to rotate within the handle assembly and includes indicia. The counting mechanism is also visible through the handle assembly. The ratchet mechanism is rotationally coupled to the counting mechanism. The ratchet mechanism includes a shaft having a having a pair of radially projecting protrusions. The aperture of the housing is configured to receive the shaft including the pair of protrusions, wherein the positioning of the shaft within the non-circular aperture of the housing inhibits multidirectional rotation of the counting mechanism. The actuator is supported on the rack bar from translation therewith. The actuator includes a protrusion projecting therefrom. The actuator is positioned to translate between a proximal position and a distal position, wherein the protrusion of the actuator engages the counting mechanism to rotate the counting mechanism, in a first direction, to adjust the indicia of the counting mechanism, visible through the handle assembly. In the proximal position, the protrusion of the actuator is disposed proximal of the counting mechanism. In the distal position, the protrusion of the actuator is disposed distal of the counting mechanism.

The counter mechanism may also further include a counter wheel including a plurality of actuation features circumferentially positioned thereabout, and a plurality of inner teeth formed circumferentially about an aperture defined through the counter wheel. The indicia may be disposed circumferentially about the counter wheel.

In some embodiments, the ratchet mechanism further includes a turning cap and a spring. The turning cap may include a plurality of teeth circumferentially positioned thereabout. The spring may be supported on the shaft of the ratchet mechanism. The ratchet mechanism may be positioned within the counter wheel of the counting mechanism, wherein the plurality of inner teeth of the counting mechanism is selectively engaged with the plurality of teeth of the ratchet mechanism. The engagement of the plurality of inner teeth of the counting mechanism and the plurality of teeth of the ratchet mechanism, together with the positioning of the shaft including the protrusions within the non-circular aperture of the housing, may prohibit multidirectional rotation of the counting mechanism.

The actuator may flex when the actuator translates between the proximal position and the distal position as the protrusion thereof engages the counting mechanism and moves distally or proximally beyond the counting mechanism. The actuator may provide a tactile or audible feedback to a user upon the actuator unflexing while translating between the proximal position and the distal position.

Other aspects, features, and advantages will be apparent from the description, the drawings, and the claims that follow.

BRIEF DESCRIPTION OF THE DRAWINGS

An illustrative embodiment of a surgical clip applier with a counter assembly is disclosed herein with reference to the drawings wherein:

FIG. 1 is a perspective view of a surgical clip applier according to the present disclosure;

FIG. 2 is an enlarged perspective view of a jaw structure of the surgical clip applier of FIG. 1;

FIGS. 4a and 4b are enlarged views of a blocking mechanism for use within the counter assembly of FIG. 3a;

FIGS. 5a and 5b are enlarged views of an alternate blocking mechanism included for use within the counter assembly of FIG. 3a;

FIG. 7 is a side view, with a half of a body removed, of a handle assembly of the surgical applier including the counter assembly of FIG. 3a.

DETAILED DESCRIPTION OF EMBODIMENTS

Figure 3A:
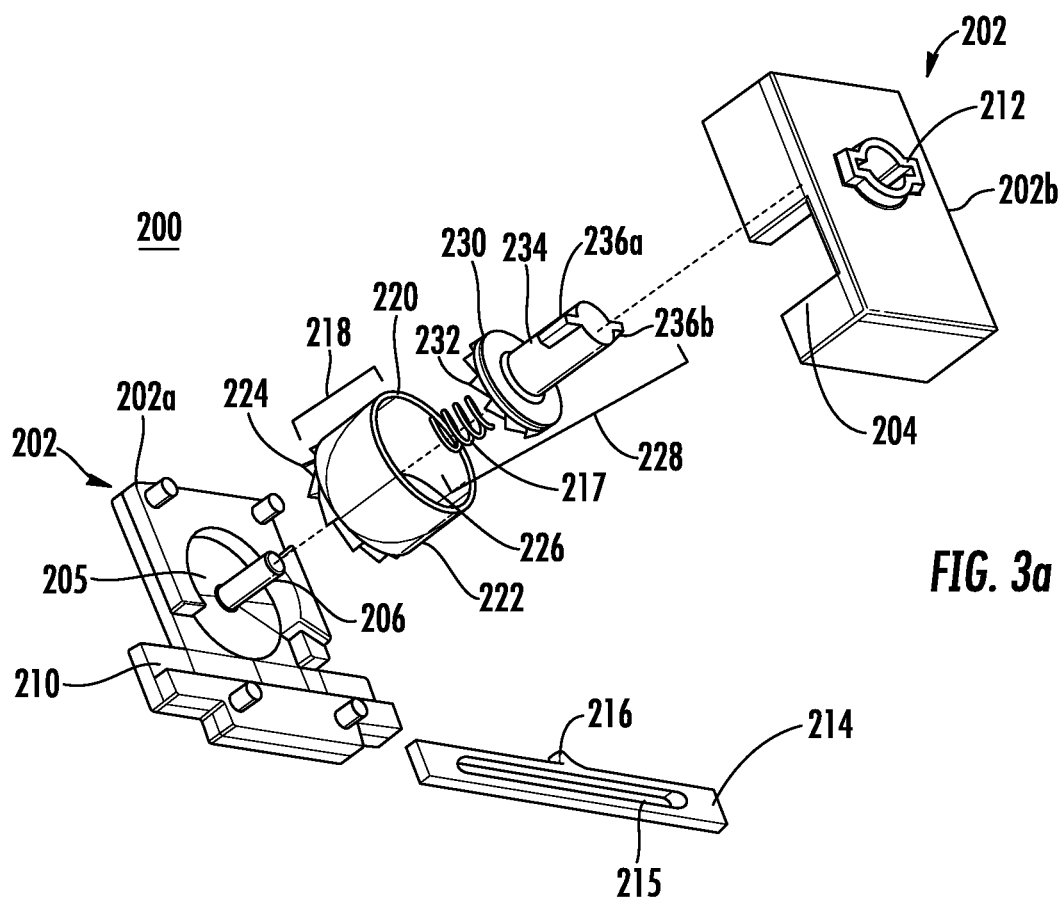
FIGS. 3a-3e are enlarged views of components of a counter assembly of the surgical clip applier of FIG. 1.

Embodiments of surgical clip appliers in accordance with the present disclosure will now be described in detail with reference to the drawing figures wherein like reference numerals identify similar or identical structural elements. As shown in the drawings and described throughout following description, as is traditional when referring to relative positioning on a surgical instrument, the term "proximal" refers to the end of the apparatus which is closer to a user and the term "distal" refers to the end of the apparatus which is further away from the user.

Figure 7:
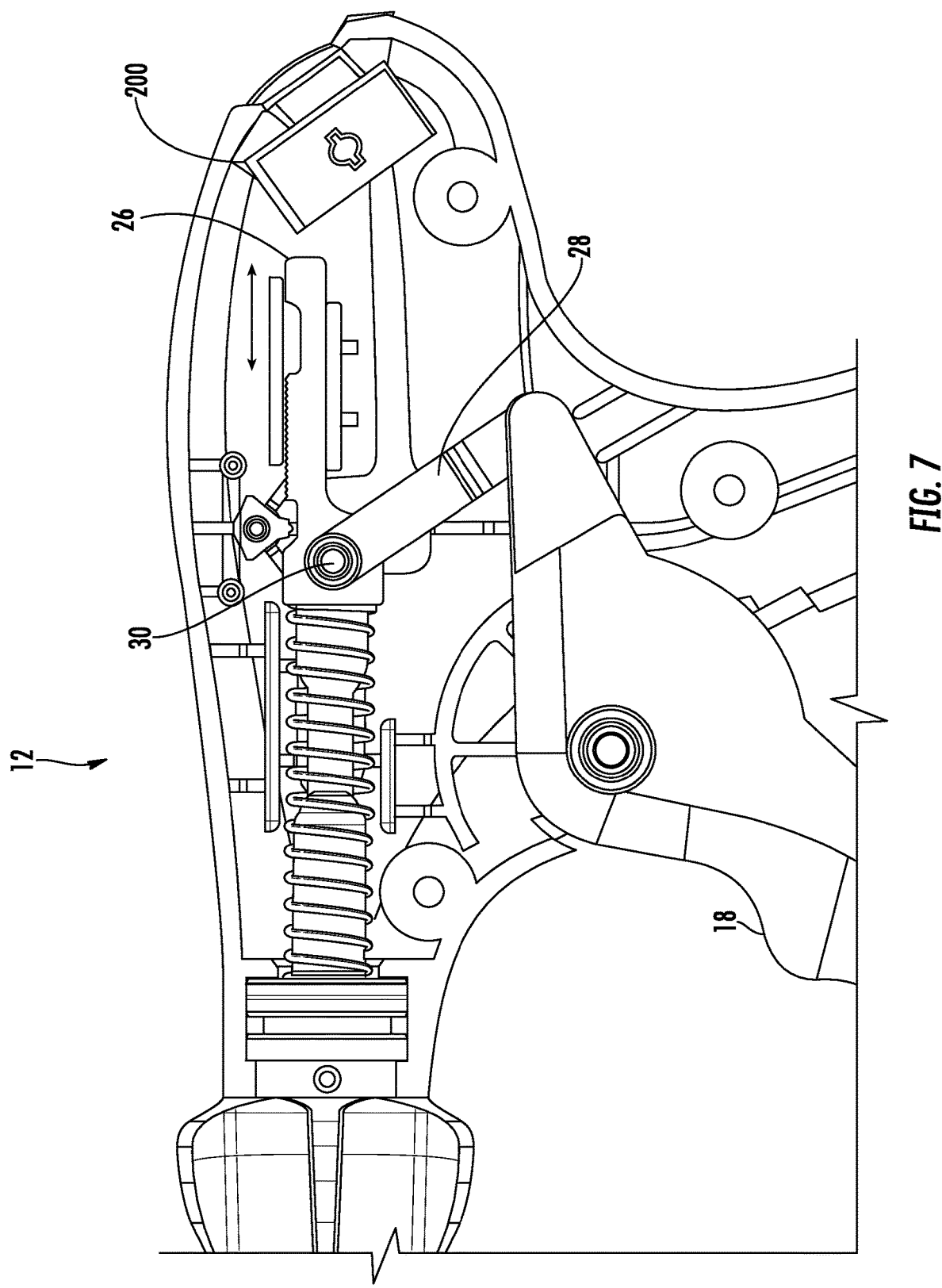

Referring now to FIGS. 1 and 2, surgical clip applier 10 generally includes a handle assembly 12 and an elongated tubular member 14 extending distally from handle assembly 12. Handle assembly 12 may be formed of a plastic material while elongated tubular member 14 may be formed of stainless steel. A pair of jaws 16 is mounted on the distal end of elongated tubular member 14 and is actuated by a trigger 18 movably mounted in handle assembly 12. The pair of jaws 16 defines a channel 22 for receipt of a surgical clip therein. The pair of jaws 16 may be formed of stainless steel or titanium. A knob 20 is rotatably mounted on a distal end of handle assembly 12 and affixed to elongated tubular member 14 to provide 360 degree rotation of elongated tubular member 14 and the pair of jaws 16 about its longitudinal axis. A counter window 24 is provided in handle assembly 12 to view an indicator, such as, for example, a counter assembly associated with handle assembly 12. The handle assembly 12 includes a longitudinally movable rack bar 26 which is connected to trigger 18 by means of a wishbone link 28 (FIG. 7). A pin 30 is provided to connect wishbone link 28 to rack bar 26. Rack bar 26 is provided for advancing and crimping a surgical clip between jaws 16 in response to actuation of trigger 18. Rack bar 26 is biased to a proximal position by a return spring. A complete description of the inner-workings and operation of surgical clip applier can be found in commonly-assigned U.S. Pat. No. 7,905,890 entitled "ENDOSCOPIC SURGICAL CLIP APPLIER" to Whitfield et al., the entire content of which is hereby incorporated by reference herein.

Moving now to FIGS. 3a-3e, a counter assembly 200, for use in surgical clip applier 10, is illustrated. Counter assembly 200 is configured to provide an indication of either the number of clips fired or the number of clips remaining within surgical clip applier 10. Counter assembly 200 includes a housing 202, an actuator 214, a counting mechanism 218, and ratchet mechanism 228.

Housing 202 of counter assembly 200 includes a first housing half 202a and a second housing half 202b. First and second housing halves 202a, 202b may be snap fitted together or connected in any other appropriate method. When connected, first and second housing halves 202a, 202b define a window 204 therein which coincides with counter window 24 of handle assembly 12. Additionally, housing 202 encases the other components of the counter assembly 200.

First housing half 202a of housing 202 defines a linear channel 210 which is configured and adapted to allow actuator 214 to translate between a proximal position and a distal position within counter assembly 200. Additionally, first housing half 202a further defines a circular recess 205 therein, which is configured and adapted to rotationally support counting mechanism 218. A stationary post 206 is centrally positioned in circular recess 205 of the first housing half 202a and extends perpendicular therefrom. Stationary post 206 facilitates connection of all the components of the counter assembly 200. Further in one embodiment, the first housing half 202a includes a blocking mechanism 208.

Second housing half 202b of housing 202 defines an aperture 212 therein that is adapted and configured to allow a shaft 234 of a ratchet mechanism 228 to pass through the second housing half 202b. Aperture 212 may be defined to have a complimentary shape to the shaft 234. Additionally in embodiments, the second housing half 202b includes a blocking mechanism 208.

Figure 3B:
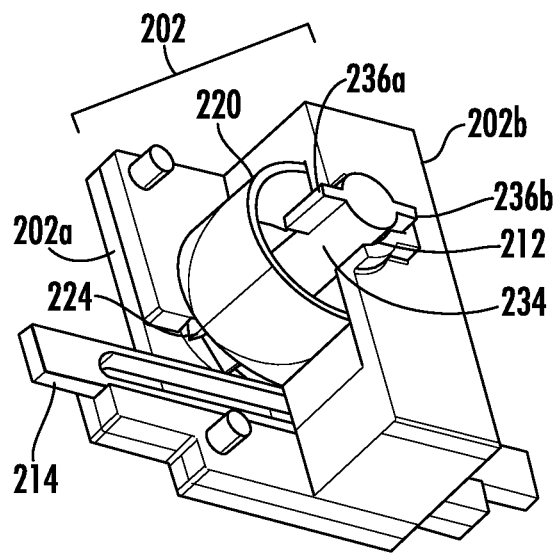
Figure 3C:
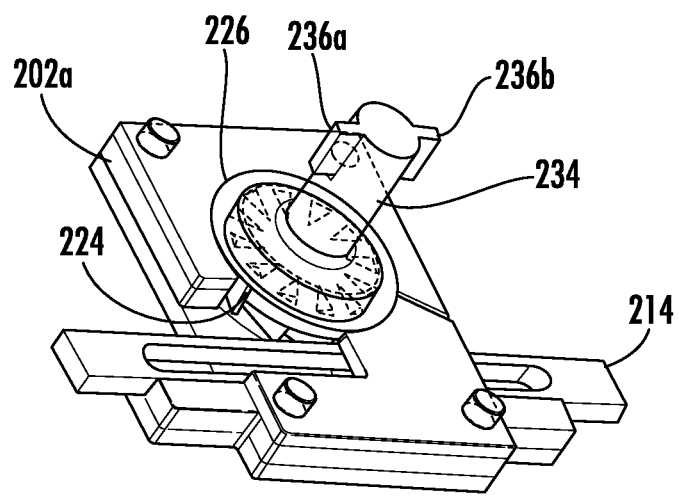
Figure 3D:
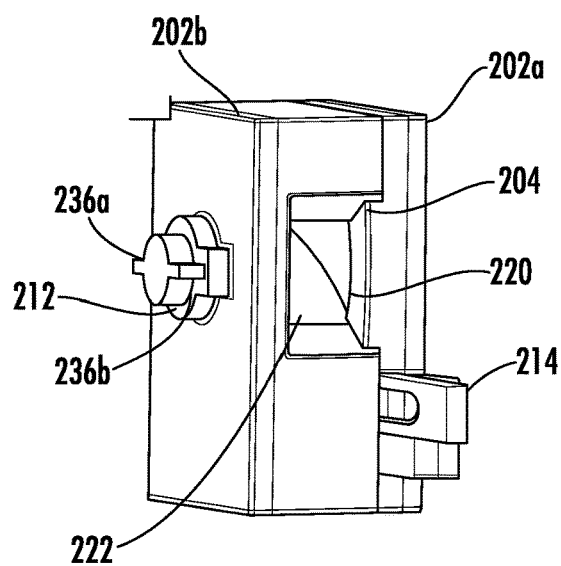
Figure 3E:
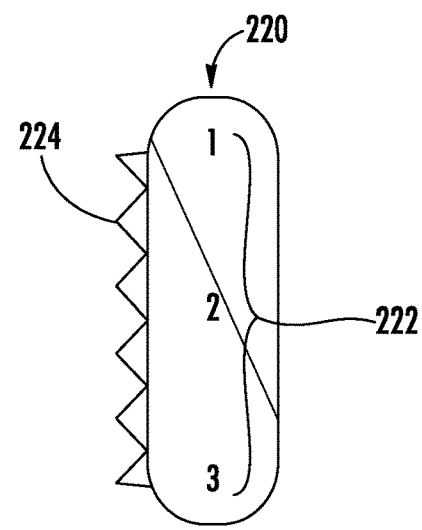

As specifically seen in FIGS. 3a and 3e, counting mechanism 218 includes a counter wheel 220 including indicia 222, actuation features 224, and inner teeth 226. In embodiments, counter wheel 220 is formed into a hollow cylinder with indicia 222 positioned or displayed circumferentially thereabout. Indicia 222 may take the form of digits, which indicate either the number of remaining surgical clips or the number of surgical clips that have been fired. Indicia 222 may take other forms, such as a color to indicate the number of surgical clips remaining. For example, the color red may indicate that a small number of surgical clips remain. Additionally, indicia 222 may include a combination of different indicia, such as alpha-numeric digits and colors. For example, as a number of indicia 222 of the counter wheel 220 increases or decreases, a color of the indicia 222 of counter wheel 220 may also change.

An aperture 221 (FIG. 6a) is defined through a center of the counter wheel 220, which is configured and dimensioned to enable counting mechanism 218 to be connected to the housing 202 of the counter assembly 200.

Actuation features 224 of counter wheel 220 may be positioned circumferentially about one side of the counter wheel 220. In some embodiments, actuation features 224 take the form of teeth, which allow the counter wheel 220 to only transition/rotate in one direction upon engagement with the actuator 214. Additionally, the profile of each of the actuation features 224 will only permit unidirectional engagement between the actuation features 224 and the actuator 214. Further, the number of actuation features 224 may be equivalent to the number of surgical clips of clip applier 10.

As seen specifically in FIGS. 3a and 3c, a plurality of inner teeth 226 are formed within an inner cavity of counter wheel 220 and arranged in a radial array. Also, the plurality of inner teeth 226 are formed circumferentially about aperture 221 of the counter wheel 220. In embodiments, each inner tooth of the plurality of inner teeth 226 may be formed into a triangular shape. Additionally, the number of inner teeth 226 is equivalent to the number of actuation features 224 of counter wheel 220, and/or the number of surgical clips of the clip applier 10.

With reference again to FIG. 3a, ratchet mechanism 228 includes, a turning cap 230 having formed thereon a plurality of teeth 232, a shaft 234 including a pair of radially projecting protrusions 236a, 236b, and spring 217. The plurality of teeth 232 of the turning cap 230 may be positioned circumferentially about one side of cap 230 in a radial array. In embodiments, the plurality of teeth 232 of turning cap 230 corresponds to the plurality of inner teeth 226 of counter wheel 220. Turning cap 230 is configured for rotational receipt within the cavity of counter wheel 220 such that the plurality of teeth 232 of turning cap 230 engage the plurality of inner teeth 226 of counter wheel 220 to inhibit the transition/rotation of counter wheel 220.

Referring to FIGS. 3b-3d, shaft 234 of ratchet mechanism 228 includes the pair of protrusions 236a, 236b. Shaft 234 is keyed to housing 202 by pair of protrusions 236a, 236b, such that shaft 234 defines a non-circular outer profile. In some embodiments, each protrusion of the pair of protrusions 236a, 236b may be formed into a winged protrusion, which extends perpendicularly from the shaft 234. Also, as illustrated, in embodiments, protrusion 236a may be positioned 180 degrees apart from protrusion 236b. As stated above, aperture 212 of housing 202 defines an opening 212a with a complimentary shape to the transverse cross-sectional profile of shaft 234 and the pair of protrusions 236a, 236b such that rotation of ratchet mechanism 228 is inhibited during rotation of counter wheel 220, while axial separation/approximation is permitted due to the shape and configuration of the plurality of teeth 232 of turning cap 230 and the plurality of inner teeth 226 of counter wheel 220. Ratchet mechanism 228 includes a spring 217, which functions to bias turning cap 230 into engagement with counter wheel 220. Additionally, spring 217 is supported on shaft 234 and is configured and dimensioned to only allow, together with the profile of inner teeth 226 of counter wheel 220 and teeth 232 of turning cap 230, unidirectional rotation of counter wheel 220.

Figure 4A:
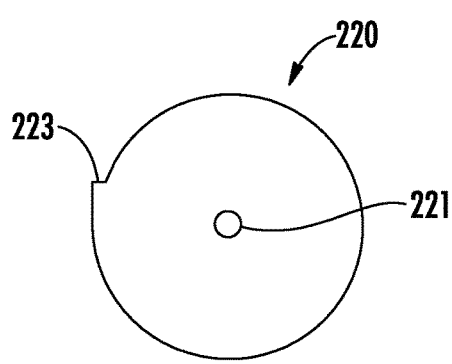
Figure 4B:
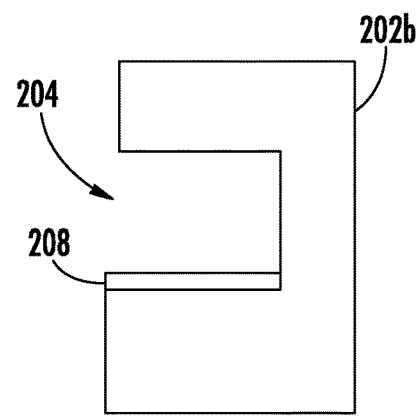

Moving briefly to FIGS. 4a and 4b, an embodiment of blocking mechanism 208 is illustrated. In this embodiment, counter wheel 220 includes a ledge 223 formed in an outer radial surface thereof. Blocking mechanism 208 is coupled to or integrally formed as part of the second housing half 202b and defines one side edge of the window 204 of housing 202. Blocking mechanism 208 includes a spring (not illustrated) that allows the blocking mechanism 208 to glide against an outer surface of the counter wheel 220 as counter wheel 220 is rotated. During rotation of counter wheel 220, when or after all the surgical clips are fired, it is envisioned that ledge 223 will come into contact with blocking mechanism 208. In this manner, ledge 223 will hinder the counter wheel 220 from rotating past the blocking mechanism 208.

Figure 5A:
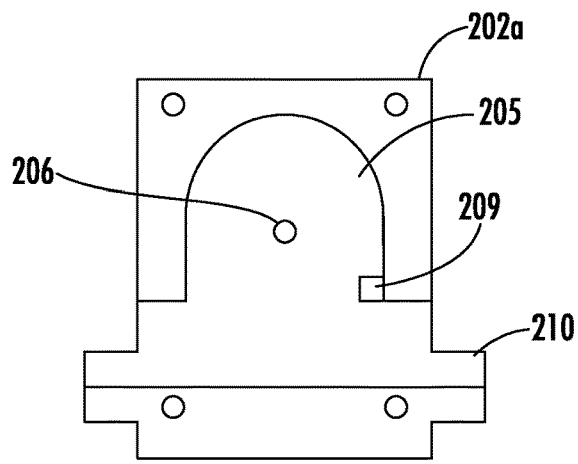
Figure 5B:
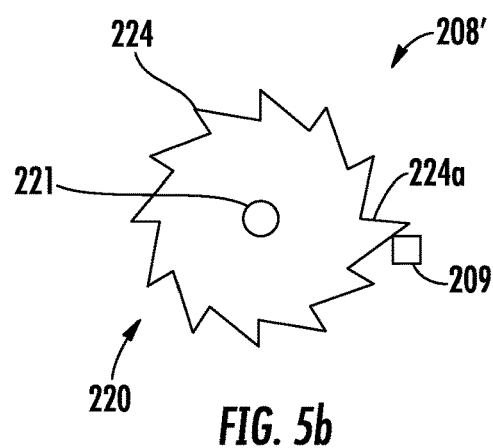

Now moving briefly to FIGS. 5a and 5b, another embodiment of a blocking mechanism is illustrated and generally identified by reference character 208'. The blocking mechanism 208' includes a blocking protrusion 209 and a plurality of actuation features 224 on counter wheel 220. In this embodiment, the blocking protrusion 209 may be located within the first housing half 202a. The blocking protrusion 209 may be positioned within the circular recess 205 of the first housing half 202a. Additionally in this embodiment, a single actuation feature 224a may project radially farther than the remainder of actuation features 224. For example, longer actuation feature 224a may be sufficiently long enough to engage with blocking protrusion 209 during use. In this embodiment, longer actuation feature 224a may be initially positioned adjacent a first side of blocking protrusion 209, and ultimately will be positioned adjacent a second side of the blocking protrusion 209 following a complete rotation of counter wheel 220, thereby prohibiting counter assembly 200 from rotating any farther. It is envisioned that the longer actuation feature 224a will reach the second side of blocking protrusion 209 when or after all the surgical clips are fired.

Referring back to FIG. 3a, a method of assembly of counter assembly 200 is illustrated. As mentioned above, all components of counter assembly 200 interconnect with one another. The stationary post 206 of the first housing half 202a extends through aperture 221 of counter wheel 220 thereby securing counting mechanism 218 to the housing 202. The stationary shaft 206 also extends into shaft 234 of ratchet mechanism 228 thereby connecting the counting mechanism 218 and the turning mechanism 228. The spring 217 of shaft 234 fits around stationary shaft 206. The shaft 234 of ratchet mechanism 228, including the pair of protrusions 236a, 236b, then extends through the aperture 212 of second housing half 202b thereby connecting the counting mechanism 218 and turning mechanism 228 to the second housing half 202b. Lastly, the first housing half 202a and the second housing half 202b are snap-fitted together thereby connecting all components of the counter assembly 200.

Figure 6A:
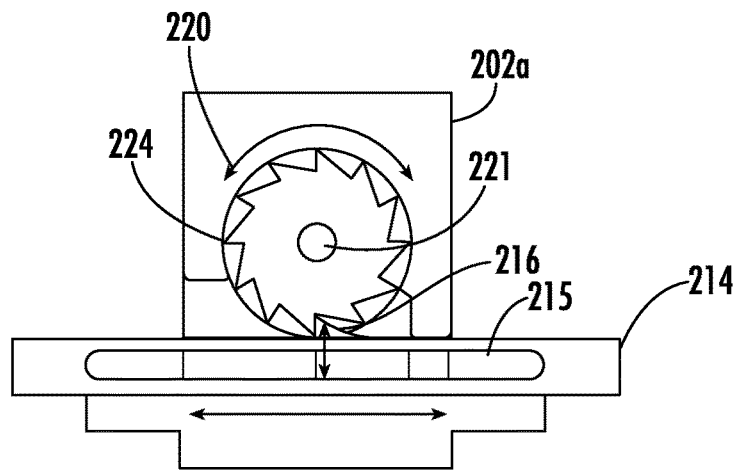
FIGS. 6a-6c are enlarged views of embodiments of an actuator of the clip applier of FIG. 1.
Figure 6B:
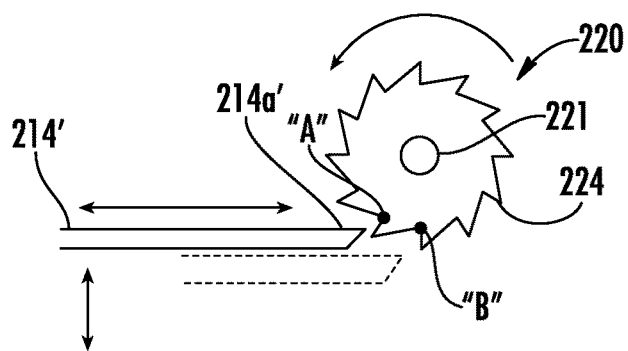
Figure 6C:
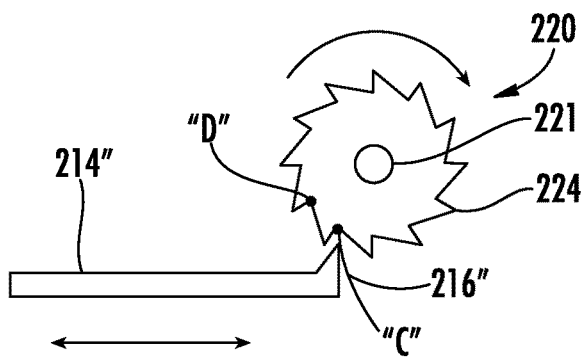

Referring to FIGS. 6a-6c, embodiments of actuator 214 are illustrated. As mentioned above, actuator 214 is coupled to rack bar 26 (FIG. 7) of clip applier 10 and translates in reaction to the translation of rack bar 26. Actuator 214 is configured and dimensioned to translate within the linear track 210 of housing 202.

In one embodiment, as illustrated in FIG. 6a, actuator 214 may include a longitudinally extending channel 215 formed therein and a protrusion 216 extending therefrom. In this embodiment, the protrusion 216 may take a triangular form (e.g., tooth). Also, protrusion 216 may be axially centrally located upon the actuator 214. Channel 215 of actuator 214 is configured and dimensioned to allow the protrusion 216 to flex/deflect an amount sufficient, while actuator 214 translates in a proximal position, such that the protrusion 216 snaps/cams past the actuation features 224 of counter wheel 220 while counter wheel 220 is held stationary by ratchet mechanism 228. Further, when actuator 214 translates in a distal direction, protrusion 216 does not flex when it engages the actuation features 224 of counter wheel 220 thereby causing counter wheel 220 to rotate as the plurality of inner teeth 226 of counter wheel 220 slip past the plurality of teeth 232 of ratchet mechanism 228. The actuator 214 is coupled to the rack bar 26. As mentioned above, the rack bar 26 is biased to the proximal position by a return spring 16 of clip applier 10, such that actuator 214 is also biased to the proximal position. The actuation of trigger 18 causes rack bar 26 to translate from a proximal position to a distal position. Upon release of trigger 18, rack bar 26 translates from the distal position back to the proximal position. Given that actuator 214 is coupled to rack bar 26, actuator 214 also translates between the proximal position and the distal position in response to the actuation and release of trigger 18. In this embodiment, when actuator 214 translates from the proximal position to the distal position, the protrusion 216 engages one of the actuation features 224 of the counter wheel 220 causing the rotation of the counter wheel 220. This rotation is caused by the linear force of the rack bar 26 and actuator 214. After the protrusion 216 engages the actuation features 224 of the counter wheel 220, actuator 214 will continue to translate to the distal position. Upon release of trigger 18, actuator 214 returns to the proximal position such that upon contact with actuation features 224, protrusion 216 flexes/deflects to pass counter assembly 200.

As described above, counter wheel 220 is configured for unidirectional rotation. The cooperation of the spring 217 supported on shaft 234, profile of the inner teeth 226 of counter wheel 220, and the teeth 232 of ratchet mechanism 228 prohibits rotation of counter wheel 220 during the translation of the protrusion 216 of actuator 214 from the distal position to the proximal position. Ratchet mechanism 228 provides a needed resistance to counter wheel 220 such that protrusion 216 is forced to flex/deflect past counter wheel 220. The actuator 214 is thus capable of translating back to the proximal position. Once actuator 214 reaches the proximal position, or as protrusion 216 thereof moves proximal to counter wheel 220, protrusion 216 of actuator 214 returns to the engaged or unflexed position.

Further, upon return to the engaged or unflexed position, the protrusion 216 provides audible/tactile feedback to the user. Protrusion 216 "snaps" back to the engaged or unflexed position, which may produces a clicking noise. Also, a user may feel protrusion 216 returning to the engaged position via trigger 18. This audible/tactile feedback indicates to the user that actuator 214, and trigger 18, has returned to the proximal position and the clip applier 10 may be fired again.

FIG. 6b illustrates another embodiment of an actuator and is generally designated by 214'. In this embodiment, actuator 214' includes a proximal end 214a'. Proximal end 214a' is configured and dimensioned to engage with counter assembly 200. Proximal end 214a' defines an end with a complimentary shape to the angle profile of the actuation features 224 of counter wheel 220.

Actuator 214' translates linearly between a proximal position and a distal position. While actuator 214' is positioned in the proximal position, the proximal end 214a' of the actuator 214' is engaged with one of the actuation features 224 of the counter wheel 220. In the distal position, the proximal end 214a' of actuator 214 is disengaged from the counter wheel 220.

As shown in FIG. 6b, upon return from the distal position to the proximal position actuator 214' begins to engage with one of the actuation features 224 of the counter wheel 220 at point "A." Actuator 214' continues to translate past point "A" forcing counter wheel 220 to rotate. Once actuator 214' reaches point "B," the proximal end 214a' of actuator 214' has reached the proximal position and will flex/deflect against the surface of counter wheel 220 of actuator 214' (as illustrated in phantom lines). When the proximal end 214a' reaches point "B," clip applier 10 may be fired again. Additionally, when the engaged actuation feature of the actuation features 224 has rotated from point "A" to point "B," the indicia 222 will be adjusted to reflect either the remaining number of surgical clips or the number of fired surgical clip.

As mentioned above, counter wheel 220 is configured for unidirectional rotation. The cooperation of the spring 217 supported on shaft 234, profile of the inner teeth 226 of counter wheel 220, and the teeth 232 of ratchet mechanism 228 prohibits rotation of counter wheel 220 during the translation of the proximal end 214a' of actuator 214' from the proximal position to the distal position.

Moving to FIG. 6c, yet another embodiment of an actuator, generally designated 214", is illustrated. Actuator 214" is very similar to actuator 214' described above, and thus, only the differences will be discussed in further detail below. Actuator 214" includes a protrusion 216" extending therefrom. Protrusion 216" may take a triangular form (e.g., tooth), which may be positioned at a proximal end 214a" of the actuator 214". The height of protrusion 216" may be any height that would allow sufficient engagement between the actuator 214" and the actuation features 224 of the counter wheel 220.

Actuator 214" translates linearly between a proximal position and a distal position. While actuator 214" is positioned in the proximal position, the protrusion 216" of actuator 214" is positioned proximally to at least one actuation feature of the actuation features 224. In the distal position, the protrusion 216" is positioned distally of the actuation features 224 of the counter wheel 220.

As shown in FIG. 6c, upon translation of actuator 214" from the proximal position to the distal position, protrusion 216" begins to engage with one of the actuation features 224 of the counter wheel 220 at point "C," e.g., the proximal position. Actuator 214" continues to translate past point "C" forcing counter wheel 220 to rotate. Once actuator 214" reaches point "D," protrusion 216" disengages with the one actuation feature of the actuation features 224 such that actuator 214" may continue to translate until actuator 214" reaches the distal position. As counter wheel 220 rotates from point "C" to point "D," indicia 222 will be adjusted to reflect either the remaining number of surgical clips or the number of fired surgical clips. The formation of a surgical clip will be completed upon actuator 214" reaching the distal position. Once actuator 214" has reached the distal position, and trigger 18 is released, and actuator 214" translates back to the proximal position.

As mentioned above, counter wheel 220 is configured for unidirectional rotation. The cooperation of the spring 217 supported on shaft 234, profile of the inner teeth 226 of counter wheel 220, and the teeth 232 of ratchet mechanism 228 prohibits rotation of counter wheel 220 during the translation of protrusion 216" of actuator 214" from point "D" to point "C". As actuator 214" translates from the distal position to the proximal positon, protrusion 216" engages against at least one actuation feature of the actuation features 224 at point "D." Protrusion 216" will "snap" back into position "C" once the actuator 214" has reached the proximal position. Further, upon return to the proximal position, the actuator 214" provides an audible/tactile feedback to the user. As mentioned above, protrusion 216" "snaps" back into point "C," which produces a clicking noise. Also, the user may feel protrusion 216" returning to point "C" via trigger 18. This audible/tactile feedback indicates to the user that actuator 214", and trigger 18, has returned to the proximal position and the clip applier 10 may be fired again.

Moving to FIG. 7, as noted above, handle assembly 12 is provided with a counter window 24 at a proximal end thereof which may reveal counter assembly 200 associated therewith. Window 204 of counter assembly 200 aligns with counter window 24 such that user may view indicia 222 during use of clip applier 10. As mentioned above, actuator 214 causes the rotation of the counter assembly 200 by using the linear force created by the transition of the rack bar 26 and actuator 214.

It should be understood that the forgoing description is only illustrative of the present clip appliers. Various alternatives and modifications can be devised by those skilled in the art without departing from the disclosure. Accordingly, the present disclosure is intended to embrace all such alternatives, modifications and variances. The embodiments described with reference to the attached drawings figures are presented only to demonstrate certain examples of the clip appliers. Other elements, steps, methods, and techniques that are insubstantially different from those described above and/or in the appended claims are also intended to be within the scope of the disclosure.

What is claimed is:

1. A surgical clip applier, comprising:
   a handle assembly;
   an elongated tubular member extending distally from the handle assembly;
   a rack bar translatably supported in the handle assembly;
   a counter assembly supported in the handle assembly and including:
      a counting mechanism positioned to rotate within the handle assembly, the counting mechanism including indicia visible through the handle assembly, a counter wheel including a plurality of actuation features circumferentially positioned thereabout, and a plurality of inner teeth formed circumferentially about an aperture defined through the counter wheel, wherein the indicia is disposed circumferentially about the counter wheel;
      a housing defining a window through which the indicia of the counting mechanism is visible during use of the surgical clip applier;
      a ratchet mechanism rotationally coupled to the counting mechanism, the ratchet mechanism prohibiting multidirectional rotation of the counting mechanism, the ratchet mechanism including:
         a turning cap including a plurality of teeth circumferentially positioned thereabout;
         a shaft extending from the turning cap, the shaft including a pair of radially projecting protrusions; and
         a spring supported on the shaft of the ratchet mechanism; and
      an actuator supported on the rack bar for translation therewith, the actuator including a protrusion projecting therefrom, the actuator positioned to translate between a proximal position and a distal position, wherein the protrusion of the actuator engages the counting mechanism to rotate the counting mechanism, in a first direction, to adjust the indicia of the counting mechanism, visible through the handle assembly, wherein in the proximal position, the protrusion of the actuator is disposed proximal of the counting mechanism, and, in the distal position, the protrusion of the actuator is disposed distal of the counting mechanism.

2. The surgical clip applier of claim 1, further including a plurality of surgical clips disposed within the elongated tubular member, wherein the indicia of the counting mechanism indicates a remaining number of the plurality of surgical clips.

3. The surgical clip applier of claim 1, wherein the ratchet mechanism is positioned within the counter wheel of the counting mechanism, wherein the plurality of inner teeth of the counting mechanism are selectively engaged with the plurality of teeth of the ratchet mechanism.

4. The surgical clip applier of claim 3, wherein the housing of the counter assembly defines an aperture therein, the aperture defining an outer transverse cross-sectional profile that is complimentary to an outer transverse cross-sectional profile of the shaft and the pair of protrusions.

5. The surgical clip applier of claim 4, wherein the engagement of the plurality of inner teeth of the counting mechanism and the plurality of teeth of the ratchet mechanism, together with the positioning of the shaft including the pair of protrusions within the aperture of the housing, prohibits multidirectional rotation of the counting mechanism.

6. The surgical clip applier of claim 2, wherein the indicia includes a plurality of numbers to indicate the remaining number of surgical clips of the plurality of surgical clips.

7. The surgical clip applier of claim 2, wherein the indicia includes a color to indicate the remaining number of surgical clips of the plurality of surgical clips.

8. The surgical clip applier of claim 1, further including a blocking mechanism coupled to the housing of the counter assembly, the blocking mechanism hindering rotation of the counting mechanism after a set number of rotations.

9. The surgical clip applier of claim 1, wherein the actuator flexes when the actuator translates between the proximal position and the distal position as the protrusion thereof engages the counting mechanism and moves distally or proximally beyond the counting mechanism.

10. The surgical clip applier of claim 1, wherein the actuator provides a tactile or audible feedback to a user upon the actuator unflexing while translating between the proximal position and the distal position.

11. A surgical clip applier, comprising:
    a handle assembly;

a rack bar translatably supported in the handle assembly;
a counter assembly supported in the handle assembly and including:
- a housing defining an aperture having a non-circular profile;
- a counting mechanism positioned to rotate within the handle assembly including indicia, the counting mechanism visible through the handle assembly;
- a ratchet mechanism rotationally coupled to the counting mechanism, the ratchet mechanism including a shaft having a pair of radially projecting protrusions, the aperture of the housing configured to receive the shaft including the pair of protrusions, wherein the positioning of the shaft within the non-circular aperture of the housing inhibits multidirectional rotation of the counting mechanism; and
- an actuator supported on the rack bar for translation therewith, the actuator including a protrusion projecting therefrom, the actuator positioned to translate between a proximal position and a distal position, wherein the protrusion of the actuator engages the counting mechanism to rotate the counting mechanism, in a first direction, to adjust the indicia of the counting mechanism, visible through the handle assembly, wherein in the proximal position, the protrusion of the actuator is disposed proximal of the counting mechanism, and, in the distal position, the protrusion of the actuator is disposed distal of the counting mechanism.

12. The surgical clip applier of claim 11, wherein the counting mechanism further includes a counter wheel including a plurality of actuation features circumferentially positioned thereabout, and a plurality of inner teeth formed circumferentially about an aperture defined through the counter wheel, wherein the indicia is disposed circumferentially about the counter wheel.

13. The surgical clip applier of claim 12, wherein the ratchet mechanism comprises:
- a turning cap including a plurality of teeth circumferentially positioned thereabout; and
- a spring supported on the shaft of the ratchet mechanism.

14. The surgical clip applier of claim 13, wherein the ratchet mechanism is positioned within the counter wheel of the counting mechanism, wherein the plurality of inner teeth of the counting mechanism are selectively engaged with the plurality of teeth of the ratchet mechanism.

15. The surgical clip applier of claim 14, wherein the engagement of the plurality of inner teeth of the counting mechanism and the plurality of teeth of the ratchet mechanism, together with the positioning of the shaft including the pair of protrusions within the non-circular aperture of the housing, prohibits multidirectional rotation of the counting mechanism.

16. The surgical clip applier of claim 11, wherein the actuator provides a tactile or audible feedback to a user upon the actuator unflexing while translating between the proximal position and the distal position.

17. The surgical clip applier of claim 11, wherein the actuator flexes when the actuator translates between the proximal position and the distal position, as the protrusion thereof engages the counting mechanism and moves distally or proximally beyond the counting mechanism.

* * * * *